United States Patent [19]
Hoek et al.

[11] Patent Number: 5,866,620
[45] Date of Patent: Feb. 2, 1999

[54] PROCESS FOR CARRYING OUT AN EXOTHERMIC REACTION

[75] Inventors: Arend Hoek, Amsterdam; Johannes Gerardus Laurijssen, The Hague, both of Netherlands

[73] Assignee: Shell Oil Company, Houston, Tex.

[21] Appl. No.: 906,738

[22] Filed: Aug. 6, 1997

[30] Foreign Application Priority Data

Aug. 8, 1996 [EP] European Pat. Off. .............. 96202236

[51] Int. Cl.⁶ .................................................. C07C 27/00
[52] U.S. Cl. ........................................... 518/700; 518/715
[58] Field of Search ..................... 518/700, 715

[56] References Cited

U.S. PATENT DOCUMENTS

| | | | |
|---|---|---|---|
| 2,567,259 | 11/1951 | Watson | 260/449 |
| 2,581,118 | 1/1952 | Main | 260/449.6 |
| 5,273,212 | 12/1993 | Gerhardus et al. | 239/132.3 |

FOREIGN PATENT DOCUMENTS

| | | | |
|---|---|---|---|
| 0 098 043 A2 | 1/1984 | European Pat. Off. | C10J 3/46 |
| 0 184 164 A2 | 6/1986 | European Pat. Off. | C10B 3/36 |
| 0 288 387 A | 4/1987 | European Pat. Off. | C01B 3/36 |
| 0 312 133 A1 | 4/1989 | European Pat. Off. | F23D 11/40 |
| 0 343 735 A2 | 11/1989 | European Pat. Off. | C01B 3/36 |

*Primary Examiner*—Gary Geist
*Assistant Examiner*—Jafar Parsa

[57] ABSTRACT

The present invention relates to a process for carrying out an exothermic reaction in the presence of a solid catalyst in a three-phase slurry reactor comprising a slurry zone and a freeboard zone, in which slurry zone the catalyst is kept in suspension in a slurry liquid, and in which freeboard zone a liquid reflux is maintained to remove catalyst from the freeboard zone and, preferably, recycling the catalyst to the slurry zone. According to a further aspect, the present invention relates to a three-phase slurry reactor adapted to the process.

10 Claims, No Drawings

PROCESS FOR CARRYING OUT AN EXOTHERMIC REACTION

FIELD OF THE INVENTION

The present invention relates to a process for carrying out an exothermic reaction in the presence of a solid catalyst in a three-phase slurry reactor. According to a further aspect, the present invention relates to a three-phase slurry reactor for carrying out an exothermic reaction.

BACKGROUND OF THE INVENTION

Three-phase slurry reactors are well known to those skilled in the art. In operation, the reactor comprises a slurry zone and a freeboard zone. In the slurry zone solid catalyst particles are kept in suspension in a liquid. The liquid serves as heat-transfer medium. The mixture of catalyst particles and liquid is commonly referred to as slurry. One or more gaseous reactants bubble through the slurry zone. The freeboard zone located above the slurry zone contains substantially no slurry and serves as a disengagement zone between slurry, and gaseous products and reactants.

The catalyst particles are typically kept in suspension by stirring or agitation by a mechanical device or, preferably, by an upward gas and/or liquid velocity.

Although substantially all catalyst particles are present in the slurry zone, a proportion of the catalyst particles escape from the slurry zone into the freeboard zone and may stick to the reactor wall or internals in the freeboard zone. In the absence of liquid heat-transfer medium, but in the presence of unreacted gaseous reactants, the said catalyst particles continue to catalyse the exothermic reaction. In this way, local hot spots are created which may damage the reactor vessel and/or internals.

Accordingly, it would be desirable to be able to remove catalyst particles efficiently from the freeboard zone.

For the purposes of this specification the term catalyst particles is intended as reference to catalyst particles per se and/or any fines thereof.

SUMMARY OF THE INVENTION

Therefore, the present invention relates to a process for carrying out an exothermic reaction in the presence of solid catalyst particles in a three-phase slurry reactor comprising a slurry zone and a freeboard zone, in which slurry zone the catalyst particles are kept in suspension in a slurry liquid, which freeboard zone contains catalyst particles escaped from the slurry zone, and in which freeboard zone a liquid reflux is maintained to remove the catalyst particles from the freeboard zone.

DETAILED DESCRIPTION

The process of the present invention provides for carrying out an exothermic reaction in the presence of solid catalyst particles in a three-phase slurry reactor. The reactor comprises a slurry zone and a freeboard zone. Catalyst particles are kept in suspension in a slurry liquid in the slurry zone and catalyst particles escaped from the slurry zone enter the freeboard zone. A liquid reflux is maintained in the freeboard zone and this liquid reflux removes the catalyst particles from the freeboard zone. Preferably, the catalyst particles in the freeboard zone are recycled to the slurry zone by means of the liquid reflux.

The liquid reflux can be generated and maintained by spraying liquid into the freeboard zone from an external source.

The liquid reflux is typically inert, that is the liquid reflux is not a reactant for the exothermic reaction and substantially does not react to other products in the process.

In one preferred embodiment, the liquid reflux from the external source is a part of the slurry liquid which is withdrawn from the slurry zone. Following separation of the said liquid from the solid particles by means known to those skilled in the art, a part of the said liquid is introduced into the freeboard zone.

According to another preferred embodiment of the invention, the exothermic reaction produces at least some gaseous products, which gaseous products are capable of at least partly condensing at a temperature between the reaction temperature in the top part of the slurry zone and 50° C. below the said reaction temperature, and the liquid reflux is generated and maintained by at least partly condensing the gaseous product in the freeboard zone.

Optionally, a combination of the above methods is employed to maintain the liquid reflux.

The gaseous products may at least partly be condensed by means known to those skilled in the art. Thus, in one embodiment the gaseous products are at least partly condensed by external cooling of the wall surrounding the freeboard zone, typically the reactor wall.

According to another embodiment, the gaseous products are at least partly condensed by allowing more leakage of heat from the freeboard zone of the reactor to the atmosphere, than from the slurry zone. This can suitably be achieved by less thermal insulation in the reactor wall surrounding the freeboard zone, relative to the reactor wall surrounding the slurry zone.

According to yet another embodiment, the gaseous products are at least partly condensed by cooling means in the freeboard zone. A variety of known cooling means may be applied, including indirect cooling means such as cooling coils.

However, a disadvantage of indirect cooling means, such as cooling coils, present in the freeboard zone is that in this way the volume of the freeboard zone occupied by internals is relatively high. Thus, the chance that a catalyst particle escaping from the slurry zone sticks to an internal in the freeboard zone, is high as well. It will be appreciated that according to a preferred embodiment, the volume of the freeboard zone occupied by internals is minimised.

Accordingly, in one preferred embodiment, the cooling in the freeboard zone is achieved by injection of a relatively cold gas, typically an inert gas. More preferably, cooling is achieved by injection of a liquid which vaporises under conditions prevailing in the freeboard zone. Thus, in this embodiment, the cooling means in the freeboard zone typically comprises gas or liquid injection means.

The cooling means in the freeboard zone is preferably controllable independent from the cooling means present in the slurry zone.

The slurry zone can be cooled by direct or indirect cooling means. For the purposes of this specification, direct cooling means refers to those means where the cooling medium is in direct contact with the slurry in the slurry zone. Indirect cooling means refers to those means where the cooling medium is not in direct contact with the slurry in the slurry zone. An example of the latter is an arrangement of cooling tubes immersed in the slurry. Preferably, the slurry zone is cooled by indirect cooling means.

It will be appreciated that in order to minimise the volume of internals present in the freeboard zone, preferably any indirect cooling means used to cool the slurry zone, hereinafter indirect slurry cooling means, substantially do not extend into the freeboard zone.

Preferably, the average temperature in the freeboard zone is decreased to a temperature which is up to 50° C. lower than the temperature in the top of the slurry zone. The temperature in the top of the slurry zone is typically the average temperature prevailing at about 5 to 15 cm below the interface between the slurry zone and the freeboard zone. More preferably, the decrease is up to 30° C.

The temperature in the freeboard zone is preferably decreased by at least 5° C., more preferably at least 10° C., relative to the temperature in the top of the slurry zone.

It will however be understood by those skilled in the art that the desired temperature decrease depends on a variety of factors such as the quantity of condensing product at a certain temperature; the amount of catalyst particles, or fines thereof, which is present in the freeboard zone; the complexity of, and volume occupied by, internals in the freeboard zone; and the average particle size of catalyst particles or fines present in the freeboard zone. Thus, it will be appreciated, it may sometimes be preferred to decrease the temperature more or less than the preferred ranges given above.

The average particle size of the catalyst particles may vary between wide limits, depending inter alia on the type of slurry zone regime. Typically, the average particle size may range from 1 µm to 2 mm, preferably from 1 µm to 1 mm.

If the average particle size is greater than 100 µm, and the particles are not kept in suspension by a mechanical device, the slurry zone regime is commonly referred to as an ebullating bed regime. Preferably, the average particle size in an ebullating bed regime is less than 600 µm, more preferably in the range from 100 to 400 µm. It will be appreciated that in general the larger the particle size of a particle, the smaller the chance that particle escapes from the slurry zone into the freeboard zone. Thus, if an ebullating bed regime is employed, primarily fines of catalyst particles will escape to the freeboard zone.

If the average particle size is at most 100 µm, and the particles are not kept in suspension by a mechanical device, the slurry zone regime is commonly referred to as a slurry phase regime. Preferably, the average particle size in a slurry phase regime is more than 5 µm, more preferably in the range from 10 to 75 µm.

If the particles are kept in suspension by a mechanical device, the slurry zone regime is commonly referred to as stirred tank regime. It will be appreciated that in principle any average particle size within the above ranges can be applied. Preferably, the average particle size is kept in the range from 1 to 200 µm.

The concentration of catalyst particles present in the slurry may range from 5 to 45% by volume, preferably, from 10 to 35% by volume. It may be desired to add in addition other particles to the slurry, as set out in for example European patent application publication No. 0 450 859. The total concentration of solid particles in the slurry is typically not more than 50% by volume, preferably not more than 45% by volume.

Suitable slurry liquids are known to those skilled in the art. Typically, at least a part of the slurry liquid is a reaction product of the exothermic reaction. Preferably, the slurry liquid is substantially completely a reaction product.

The exothermic reaction is a reaction which is carried out in the presence of a solid catalyst, and which is capable of being carried out in a three-phase slurry reactor. Typically, at least one of the reactants of the exothermic reaction is gaseous. Examples of exothermic reactions include hydrogenation reactions, hydroformylation, alkanol synthesis, the preparation of aromatic urethanes using carbon monoxide, Kölbel-Engelhardt synthesis, polyolefin synthesis, and Fischer-Tropsch synthesis. According to a preferred embodiment of the present invention, the exothermic reaction is a Fischer-Tropsch synthesis reaction.

The Fischer-Tropsch synthesis is well known to those skilled in the art and involves synthesis of hydrocarbons from a gaseous mixture of hydrogen and carbon monoxide, by contacting that mixture at reaction conditions with a Fischer-Tropsch catalyst.

Products of the Fischer-Tropsch synthesis may range from methane to heavy paraffinic waxes. Preferably, the production of methane is minimised and a substantial portion of the hydrocarbons produced have a carbon chain length of at least 5 carbon atoms. Preferably, the amount of C5+ hydrocarbons is at least 60% by weight of the total product, more preferably, at least 70% by weight, even more preferably at least 80% by weight, most preferably at least 85% by weight.

Fischer-Tropsch catalysts are known in the art, and typically include a Group VIII metal component, preferably cobalt, iron and/or ruthenium, more preferably cobalt. Typically, the catalysts comprise a catalyst carrier. The catalyst carrier is preferably porous, such as a porous inorganic refractory oxide, more preferably alumina, silica, titania, zirconia or mixtures thereof.

The optimum amount of catalytically active metal present on the carrier depends inter alia on the specific catalytically active metal. Typically, the amount of cobalt present in the catalyst may range from 1 to 100 parts by weight per 100 parts by weight of carrier material, preferably from 10 to 50 parts by weight per 100 parts by weight of carrier material.

The catalytically active metal may be present in the catalyst together with one or more metal promoters or co-catalysts. The promoters may be present as metals or as the metal oxide, depending upon the particular promoter concerned. Suitable promoters include oxides of metals from Groups IIA, IIIB, IVB, VB, VIB and/or VIIB of the Periodic Table, oxides of the lanthanides and/or the actinides. Preferably, the catalyst comprises at least one oxide of an element in Group IVB, VB and/or VIIB of the Periodic Table, in particular titanium, zirconium, manganese and/or vanadium. As an alternative or in addition to the metal oxide promoter, the catalyst may comprise a metal promoter selected from Groups VIIB and/or VIII of the Periodic Table. Preferred metal promoters include rhenium, platinum and palladium.

A most suitable catalyst comprises cobalt as the catalytically active metal and zirconium as a promoter. Another most suitable catalyst comprises cobalt as the catalytically active metal and manganese and/or vanadium as a promoter.

The promoter, if present in the catalyst, is typically present in an amount of from 0.1 to 60 parts by weight per 100 parts by weight of carrier material, preferably from 0.5 to 40 parts by weight per 100 parts by weight of carrier material. It will however be appreciated that the optimum amount of promoter may vary for the respective elements which act as promoter. If the catalyst comprises cobalt as the catalytically active metal and manganese and/or vanadium as promoter, the cobalt:(manganese +vanadium) atomic ratio is advantageously at least 12:1.

The Fischer-Tropsch synthesis is preferably carried out at a temperature in the range from 125° to 350° C., more preferably 175° to 275° C., most preferably 200° to 260° C. The pressure preferably ranges from 5 to 150 bar abs., more preferably from 5 to 80 bar abs.

Hydrogen and carbon monoxide (synthesis gas) is typically fed to the three-phase slurry reactor at a molar ratio in the range from 0.4 to 2.5. Preferably, the hydrogen to carbon monoxide molar ratio is in the range from 1.0 to 2.5.

The gaseous hourly space velocity may vary within wide ranges and is typically in the range from 1500 to 10000 Nl/l/h, preferably in the range from 2500 to 7500 Nl/l/h.

The Fischer-Tropsch synthesis is preferably carried out in a slurry phase regime or an ebullating bed regime, wherein the catalyst particles are kept in suspension by an upward superficial gas and/or liquid velocity.

It will be understood that the skilled person is capable to select the most appropriate conditions for a specific reactor configuration and reaction regime.

Preferably, the superficial gas velocity of the synthesis gas is in the range from 0.5 to 50 cm/sec, more preferably in the range from 5 to 35 cm/sec.

Typically, the superficial liquid velocity is kept in the range from 0.001 to 4.0 cm/sec, including liquid production. It will be appreciated that the preferred range may depend on the preferred mode of operation. According to one preferred embodiment, the superficial liquid velocity is kept in the range from 0.005 to 1.0 cm/sec.

As outlined hereinabove, preferably the volume of the freeboard zone occupied by internals is minimised. In this way, the chance that a catalyst particle escaping from the slurry zone sticks to an internal in the freeboard zone, is minimised as well.

However, it may be preferred that the freeboard zone contains means specifically designed to trap catalyst particles. Such means e.g. may be used for protecting parts of the freeboard zone which are difficult to clean with a liquid reflux or otherwise, for example outlet means for gases.

According to a further aspect, the present invention relates to a three-phase slurry reactor for carrying out exothermic reactions in the presence of a catalyst, comprising reactant inlet means and product outlet means, a slurry zone equipped with slurry cooling means, and a freeboard zone, wherein the reactor is adapted to maintain a liquid reflux in the freeboard zone.

Typically, the three-phase slurry reactor is specifically adapted to the process of the present invention. Thus, it will be understood by those skilled in the art that preferred embodiments discussed in relation to the process are also preferred embodiments with respect to the three-phase slurry reactor.

We claim:

1. A process for carrying out an exothermic reaction in the presence of solid catalyst particles in a three-phase slurry reactor comprising a slurry zone and a freeboard zone, in which slurry zone the catalyst particles are kept in suspension in a slurry liquid, which freeboard zone contains catalyst particles escaped from the slurry zone, and in which freeboard zone a liquid reflux is maintained to remove the catalyst particles from the freeboard zone.

2. A process as claimed in claim 1, wherein the catalyst particles present in the freeboard zone are recycled to the slurry zone.

3. A process for carrying out an exothermic reaction as claimed in claim 1, which exothermic reaction produces at least some gaseous products, which gaseous products are capable of at least partly condensing at a temperature between the reaction temperature in the top part of the slurry zone and 50° C. below the said reaction temperature, wherein the gaseous product is at least partly condensed in the freeboard zone to generate the liquid reflux.

4. A process as claimed in claim 3, wherein the gaseous products are at least partly condensed by external cooling of the wall surrounding the freeboard zone.

5. A process as claimed in claim 3, wherein the gaseous products are at least partly condensed by allowing leakage of heat from the freeboard zone of the reactor, such that the temperature in the freeboard zone is decreased relative to the temperature in the top of the slurry zone.

6. A process as claimed in claim 3, wherein the gaseous products are at least partly condensed by cooling means in the freeboard zone.

7. A process as claimed in claim 1, wherein the exothermic reaction is a Fischer-Tropsch synthesis reaction.

8. A process as claimed in claim 1, wherein indirect slurry cooling means used to cool the slurry zone substantially does not extend into the freeboard zone.

9. A process as claimed in claim 1, wherein the freeboard zone contains means to trap catalyst particles.

10. A process as claimed in claim 9, wherein the means to trap catalyst particles comprises one or more corrugated plates and a liquid reflux is maintained over the corrugated plates.

* * * * *